United States Patent [19]

Allen et al.

[11] 4,306,879

[45] Dec. 22, 1981

[54] CHEMICAL LOGGING OF GEOTHERMAL WELLS

[75] Inventors: Charles A. Allen; Richard E. McAtee, both of Idaho Falls, Id.

[73] Assignee: The United States of America as represented by the United States Department of Energy, Washington, D.C.

[21] Appl. No.: 105,337

[22] Filed: Dec. 19, 1979

[51] Int. Cl.$^3$ ............................................. G01N 33/24
[52] U.S. Cl. ............................................... 23/230 EP
[58] Field of Search .................... 23/230 EP; 166/250

[56] References Cited

U.S. PATENT DOCUMENTS 2,336,613 12/1943 Horvitz ........................... 23/230 EP
3,801,281 4/1974 Thompson et al. ............ 23/230 EP

OTHER PUBLICATIONS

Petroleum Exploration Handbook, 1961, Moody, McGraw-Hill pp. 13-10 to 13-15, 21-8 to -21-13.
Geochemical Prospecting for Petroleum and Natural Gas, Kartsev A.A. et al., pp. 250-254, 260-273.

Primary Examiner—Michael S. Marcus
Attorney, Agent, or Firm—James W. Weinberger; Frank H. Jackson; Richard G. Besha

[57] ABSTRACT

The presence of geothermal aquifers can be detected while drilling in geothermal formations by maintaining a chemical log of the ratio of the concentrations of calcium to carbonate and bicarbonate ions in the return drilling fluid. A continuous increase in the ratio of the concentrations of calcium to carbonate and bicarbonate ions is indicative of the existence of a warm or hot geothermal aquifer at some increased depth.

2 Claims, 2 Drawing Figures

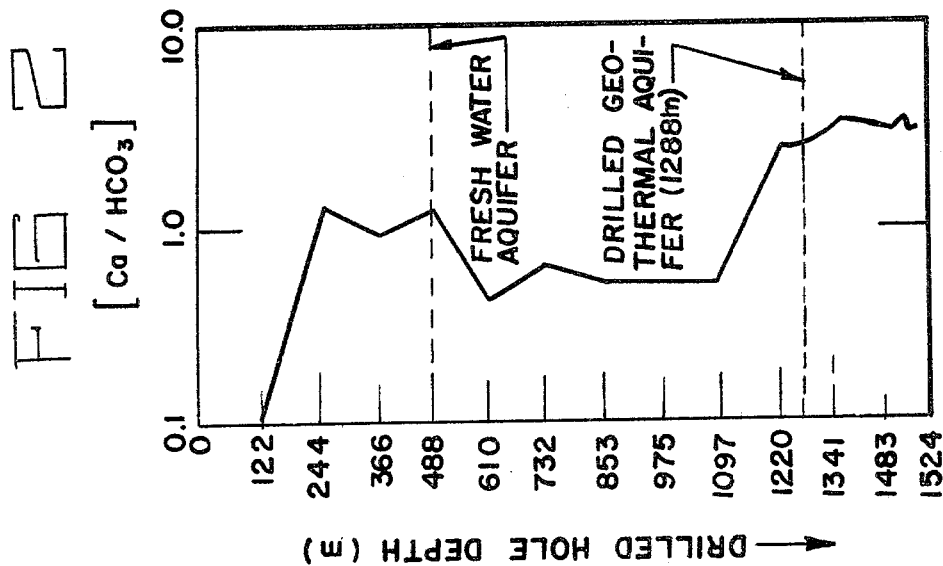
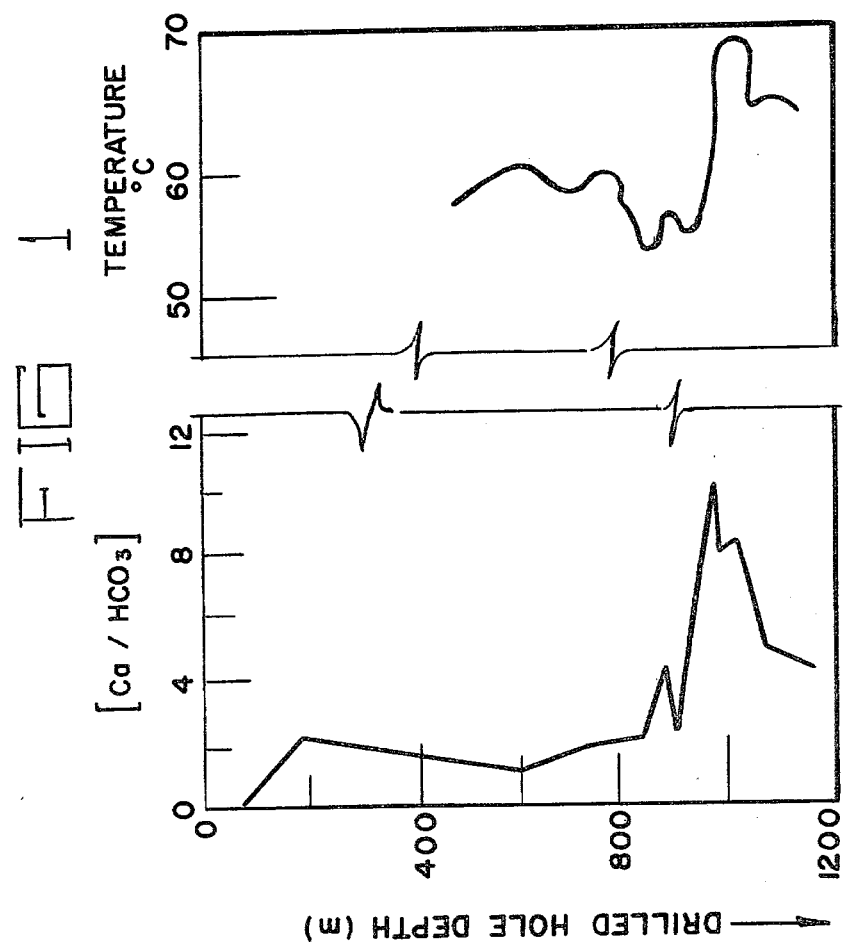

CHEMICAL LOGGING OF GEOTHERMAL WELLS

CONTRACTUAL ORIGIN OF THE INVENTION

The invention described herein was made in the course of, or under, a contract with the UNITED STATES DEPARTMENT OF ENERGY.

BACKGROUND OF THE INVENTION

This invention relates to a method of chemical logging of wells drilled in geothermal formations. More specifically, this invention relates to a method of maintaining and monitoring a chemical log during a well drilling operation to detect the presence of geothermal aquifers before the aquifer is penetrated by the drill.

Growing concern over shortages of fossil fuel has led to increased emphasis on finding and developing new sources of thermal energy such as that which is available in certain geological formations throughout the world. These formations, called geothermal reservoirs, contain usable quantities of warm or hot water in underground aquifers reasonably near enough to the earth's surface to be recoverable. These geothermal aquifers can provide energy for driving electrical generators, for space heating and for performing other energy functions. The growth of the geothermal industry has created a need for techniques which can be used, during drilling operations, to assist in the determination of well depth, casing location and well development.

When drilling wells in geothermal formations, it is usually desirable to be able to detect the presence of a warm or hot water aquifers before the aquifer has been penetrated by the drill bit for several reasons. It permits the setting of well casing in place in the borehole in time to prevent possible contamination of any fresh water aquifers already penetrated by the drill string with upwelling geothermal water which often contains undesirable minerals such as large quantities of sodium chloride or low levels of fluorine on sulfur. Wells are drilled using either a mud or water, as a drilling fluid. Mud is preferred since it reduces the amount of water which must otherwise be used, seals off porous areas in the earth to prevent loss of water, lubricates the drill bit and flushes rock cuttings from the borehole better than water. However, penetration of a potentially productive geothermal aquifer by the drill bit while using mud as the drilling fluid could result in the aquifer being wholly or partially sealed by contact of the mud on the warm porous rock formation. This could result in the loss of the aquifer as source of geothermal energy. Thus, knowledge of the existence of an aquifer in time to permit discontinuance of the use of mud, could prevent loss of a productive aquifer.

A chemical log of a well is a profile of the concentration of chemical elements found in the various geological formation fluids relative to the depth at which they were found. This profile may include elements such as $Cl^{31}$, $F^-$, $Na^+$, $Ca^{++}$, and $SiO_2$ in addition to conductivity and pH of the water. The log is prepared by analyzing the drill return fluid at predetermined depths, for example every 10 to 20 meters, and plotting the concentrations of the various analyzed chemical species relative to the drill depth at which the concentrations were present. The log is useful for obtaining information as to what type of aquifer the drill bit has penetrated, the relative temperature of the aquifer and the composition of the aquifer water. However, up until now, the log has not been useful for determining the existence of a geothermal aquifer before it has been penetrated by the drill bit.

SUMMARY OF THE INVENTION

A method has been developed by which the presence of a geothermal aquifer, can be detected during drilling operations in a geothermal formation before the aquifer has been penetrated by the drill bit. By the method of the invention, the return drilling fluid recovered from predetermined depths during the drilling operation is analyzed to determine the concentration of calcium, and bicarbonate ions in the fluid, a log is maintained of the ratio of the concentrations of calcium ions to bicarbonate ions relative to the drill depth at which these concentrations were present, and the log is monitored to observe any changes in the ratio of the concentrations of calcium to bicarbonate ions whereby a continuously increasing ratio of the concentrations of calcium ions to bicarbonate ions is indicative of the presence of a geothermal aquifer at some greater depth.

As used herein, the term geothermal aquifer refers to a porous zone in the earth's crust which contains water which is at least about 60° C.

It is therefore one object of the invention to provide a method for detecting the presence of a geothermal aquifer during drilling operations in a geothermal formation before the aquifer is penetrated by the drill bit.

It is the other object of the invention to provide a method of chemical logging a well being drilled in a geothermal formation in order to detect the presence of a geothermal aquifer before the aquifer is penetrated by the drill bit.

BRIEF DESCRIPTION OF THE DRAWINGS

FIG. 1 compares a temperature log to a log of the ratio of calcium to bicarbonate ion concentration at the same depths in Well RRGI-6 at the Raft River Geothermal Test Site in Idaho.

FIG. 2 is a log of the ratio of calcium to bicarbonate ion concentration in Well RRGP-5 at the Raft River Geothermal Test Site in Idaho showing the depth at which a fresh water aquifer and a geothermal aquifer were penetrated.

DETAILED DESCRIPTION OF THE PREFERRED EMBODIMENT

These and other objects of the invention may be met by analyzing the return drilling fluid obtained from predetermined depths during the drilling operation to determine the concentration of calcium, carbonate and bicarbonate ions, maintaining a log of the ratio of the concentration of calcium ion to the sum of the concentrations of carbonate and bicarbonate ions relative to the drill depth of the hole at which the concentrations were present, and monitoring the log to observe any changes in the ratio of the concentrations of calcium to carbonate and bicarbonate ions, whereby a continuously increasing ratio of the concentration of calcium, to carbonate and bicarbonate ions in the return drilling fluid is indicative of the presence of a geothermal aquifer at some greater depth.

The drill return fluid is analyzed for calcium, carbonate and bicarbonate ions at predetermined intervals of change in drill bit depth. For example, samples may be made every 30 meters during the first part of the drilling and then increased to every 10 to 20 meters when approaching potential aquifer locations. It may be necessary, if drilling mud is being used, to separate the drilling mud and other residues from the water sample by any convenient method such as by centrifuging and filtering. In some cases, the centrifuge may not settle the gelatinous mud suspension and filtering through a coarse filter may be necessary. The samples may be analyzed for calcium, carbonate and bicarbonate concentration by any suitable analytical technique. Satisfactory results were obtained using the procedures described by Brown, Skougstad and Fishman in *Techniques of Water-Resources Investigations of the USGS*, Washington, D.C., 1970, Book 5, Chapter A1, Part IV.

While it is possible to accurately detect the presence of geothermal water by monitoring the ratio of the concentrations of calcium to bicarbonate ion alone as is shown by the logs in FIGS. 1 and 2, it has been found that the presence of drilling mud during the drilling operation has a tendency to distort this ratio. The physical characteristics of the drill mud, such as viscosity, weight, density and thickness, are partially controlled by pH. The pH of the drill fluid when drill mud is used generally ranges between 9 and 11.5. When water alone is used as the drill fluid, the pH is normally about 7.5 to 8.5 and bicarbonate ions are the dominant species. Bicarbonate shifts to carbonate ion at about a pH of 11 to 12. Therefore, it has been found more accurate, at least when drill mud is present, to determine the calcium to carbonate plus bicarbonate plus bicarbonate ratio.

Chemical composition changes from geothermal water intrusion are not definable except for the increase in Ca—$HCO_3$ ratio and decrease in alkalinity. Freshwater intrusion into the drill water would generally increase hardness and alkalinity and decrease $F^-$, $Cl^-$, conductivity and the calcium-bicarbonate ratio. A geothermal and fresh-water mixture intrusion into the drill water would result in increases in the calcium-bicarbonate ratio. The changes in the other chemical species would not be definable.

While we do not wish to be bound by this explanation, it appears that the displacement uphole of the calcium to carbonate and bicarbonate ratio is due to the leakage or diffusion of the hot water from the aquifer into the less porous rock strata above the aquifer. This uphole displacement has varied between 25 and 120 meters for the test so far. The amount of displacement appears to be a function of the permeability of the material above the aquifer, so that a more porous material would provide a greater uphole displacement.

Although the concentration of calcium carbonate and bicarbonate ions may vary widely between various geothermal formations, the ratio of the concentrations of calcium to bicarbonate or to bicarbonate plus carbonate ions seems to vary substantially less between geological formations. Nevertheless, it is the trend of the increasing ratio of the concentrations of calcium to bicarbonate and carbonate ions which indicates the presence of the geothermal aquifer.

The following Examples are given to illustrate the invention, but are not to be taken as limiting the scope of the invention which is defined by the appended claims.

EXAMPLE I

A well, designated as RRGI-6, was drilled at the Raft River Geothermal Test Site in South Central Idaho. As the well was drilled samples were collected from the drill return fluid at specified intervals of change in the drill string length. The drill fluid was pumped from the mud pit through the drill string and returned up borehole between the borehole walls and the drill stem. Drill fluid samples were collected at the point where the drill return fluid flowed into the mud pit. Samples of the drill fluid returns were taken at 120 m intervals of drilling depth to a depth of 910 meters and then even 60 meters to total depth. Samples of 4–5 liters were collected during the period of the drilling operation when drilling mud was used to assure an adequate sample. Once the borehole was cased and only water was used for a circulating medium, one-liter samples were collected. The drilling mud and other residues were separated from the water sample by centrifuging and filtering. In cases where the centrifuge would not settle the gelatinous mud suspension, a coarse filter was used. The samples were analyzed for conductivity, pH, carbonate, bicarbonate, $Cl^-$, $F^-$, $Ca^{++}$, and $SiO_2$ by the procedures described by Brown, Skougstad and Fishman.

A chemical log was then prepared by plotting graphically the ratio of the concentration of calcium to bicarbonate ion to the drill string depth. The resulting log is a profile of the chemical changes taking place in the drill fluid during the drilling operation.

FIG. 1 is a profile of the calcium to bicarbonate ratio of Well RRGI-6 compared with a temperature profile of the same well. As shown in FIG. 1, a comparison of the calcium to bicarbonate ratio to the temperature log reveals that they are similar except that the calcium-bicarbonate log is displaced uphole about 60 m. This means that the chemical log anticipated the geothermal aquifer 60 m before the drill penetrated it.

EXAMPLE II

A second well, designated RRGP-5, was drilled at the Raft River Geothermal Site. Sampling intervals were 120 m until changes were observed in the chemical log to indicate increasing temperature. When a temperature increase was detected, the sampling interval was decreased to 60 m. The resulting calcium to bicarbonate chemical log is shown in FIG. 2. Evaluation of the calcium-bicarbonate log reveals a sharp increase in temperature at 1220 m of depth. This increase in the calcium to bicarbonate ratio continued until the drill string reached 1280 m of depth, when a flow of hot water was detected. The flow rate was estimated to be approximately 4100 l/minute at about 275° F. Note that the chemical log indicated the presence of this geothermal aquifer about 100 m before the drill penetrated the geothermal aquifer. Note also that the chemical log indicated the existence of the fresh water aquifer at 488 m.

As can be seen, the chemical log of the ratio of the concentration of calcium to the sum of the concentration of carbonate plus bicarbonate ion shows excellent results in the ability to anticipate the existence of geothermal aquifers in sufficient time to set casings and to take other such protective measures as are necessary to protect the productivity of the aquifer.

The embodiments of the invention in which an exclusive property or privilege is claimed are defined as follows:

1. A method of detecting the presence of a geothermal aquifer while drilling a well in a geothermal formation, before the formation water is penetrated, comprising:
   analyzing the return drilling fluid recovered from predetermined depths during the drilling operation to determine the concentration of calcium and bicarbonate ions;

maintaining a log of the ratio of the concentration of calcium ion to bicarbonate ion relative to the drill depth of the hole at which the concentrations were present; and monitoring the log to observe any changes in the ratio of the concentrations of the calcium to bicarbonate ion, whereby a continuously increasing ratio of the concentrations of calcium to bicarbonate ion is indicative of the presence of a geothermal aquifer at some greater depth.

2. The method of claim 1 wherein the return drilling fluid is also analyzed for carbonate ion, the log is maintained of the ratio of the concentrations of calcium ion to the sum of the concentrations of carbonate and bicarbonate ions, and a continuously increasing ratio of the concentration of calcium to the sum of the concentrations of carbonate and bicarbonate ions indicative of the presence of a geothermal aquifer.

* * * * *